(12) United States Patent
Huang et al.

(10) Patent No.: US 9,210,308 B2
(45) Date of Patent: Dec. 8, 2015

(54) MEASURING APPARATUS AND MEASURING METHOD THEREOF

(71) Applicants: Jiun-Ping Huang, Taichung (TW);
Chih-Jung Chang, Taichung (TW);
Tung-Shen Chen, Taichung (TW)

(72) Inventors: Jiun-Ping Huang, Taichung (TW);
Chih-Jung Chang, Taichung (TW);
Tung-Shen Chen, Taichung (TW)

(73) Assignee: Genius Electronic Optical Co., Ltd., Central Taiwan Science Park, Daya District, Taichung (TW)

(*) Notice: Subject to any disclaimer, the term of this patent is extended or adjusted under 35 U.S.C. 154(b) by 65 days.

(21) Appl. No.: 14/289,655

(22) Filed: May 29, 2014

(65) Prior Publication Data

US 2015/0264227 A1  Sep. 17, 2015

(30) Foreign Application Priority Data

Mar. 12, 2014  (TW) .............................. 103108745 A

(51) Int. Cl.
*G01N 21/55*  (2014.01)
*H04N 5/225*  (2006.01)
*G02B 7/04*  (2006.01)
*G02B 27/64*  (2006.01)
*G02B 27/30*  (2006.01)
*G02B 27/14*  (2006.01)

(52) U.S. Cl.
CPC ............... *H04N 5/2252* (2013.01); *G02B 7/04* (2013.01); *G02B 27/646* (2013.01); *H04N 5/2253* (2013.01); *G01N 21/55* (2013.01); *G02B 27/144* (2013.01); *G02B 27/30* (2013.01)

(58) Field of Classification Search
CPC ........ G02B 27/646; G02B 7/08; G02B 7/023;
G02B 27/0075; G02B 7/02; G02B 7/04;
G02B 7/09; G02B 7/102; G02B 13/0015;
G02B 13/007; G02B 13/0075; G02B 13/009;
G02B 21/002; G02B 21/367; G02B 23/02
See application file for complete search history.

(56) References Cited

U.S. PATENT DOCUMENTS

2012/0138586 A1* 6/2012 Webster ................. A61B 18/20
219/121.64
2012/0320384 A1* 12/2012 Hsu ........................ G01B 11/26
356/614

* cited by examiner

*Primary Examiner* — Michael P Stafira
(74) *Attorney, Agent, or Firm* — Winston Hsu; Scott Margo

(57) ABSTRACT

A measuring apparatus for measuring a voice-coil-motor focusing device having a magnet holder and a coil carrier movably disposed in the magnet holder includes a current device, an image capturing device, a collimator, a half-reflecting mirror, a reflecting mirror, and an optical sensing device. The image capturing device captures images of the coil carrier during the coil carrier is driven by the current device to move transversely to calculate displacement data of the coil carrier. Light of the collimator is reflected to the coil carrier by the half-reflecting mirror and then reflected back to the half-reflecting mirror by the reflecting mirror. The optical sensing device detects light reflected by the half-reflecting mirror during the coil carrier is driven by the current device to move transversely to calculate tilt-angle data of the coil carrier.

12 Claims, 4 Drawing Sheets

MEASURING APPARATUS AND MEASURING METHOD THEREOF

BACKGROUND OF THE INVENTION

1. Field of the Invention

The present invention relates to a measuring apparatus and a measuring method thereof, and more specifically, to a measuring apparatus for measuring a voice-coil-motor focusing device and a measuring method thereof.

2. Description of the Prior Art

In general, a voice coil motor is wildly applied to autofocusing of a lens assembly of a camera. The conventional mechanical design is to mount a coil carrier in a magnet holder in a longitudinally movable manner and then mount the lens assembly on the coil carrier. Accordingly, once the coil carrier is electrified, coils wound around the coil carrier could receive force in a magnetic field generated by magnets disposed on the magnet holder to drive the coil carrier to move longitudinally relative to the magnet holder for adjusting the position of the lens assembly of the camera, so as to achieve the autofocusing purpose. In practical application, the voice coil motor usually has an anti-shake function to further improve the image capturing quality of the camera. The conventional design is to dispose additional coils on the coil carrier to drive the coil carrier to move transversely relative to the magnet holder. In such a manner, when transverse movement of the coil carrier occurs during the voice coil motor is operated in a vibration environment, the additional coils could be electrified to receive force in the magnetic field generated by the magnets disposed on the magnet holder for driving the coil carrier to move in an opposite direction. Accordingly, the aforesaid opposite movement of the coil carrier could compensate for the transverse movement of the coil carrier due to vibration, so as to achieve the anti-shake purpose.

However, since there is no appropriate measuring apparatus to measure the performance of the anti-shake function of the voice coil motor, a manufacturer could not precisely know whether the performance of the anti-shake function of the voice coil motor conforms to its product needs.

SUMMARY OF THE INVENTION

An objective of the present invention is to provide a measuring apparatus for measuring a voice-coil-motor focusing device and a measuring method thereof, to solve the aforesaid problem.

The present invention provides a measuring apparatus for measuring a voice-coil-motor focusing device. The voice-coil-motor focusing device includes a magnet holder and a coil carrier. The coil carrier is movably disposed in the magnet holder. The measuring apparatus includes a base, a platform, a current device, an image capturing device, a collimator, a first half-reflecting mirror, a first reflecting mirror, and an optical sensing device. The platform is disposed on the base for placing the voice-coil-motor focusing device. The current device is electrically connected to the voice-coil-motor focusing device for providing current to drive the coil carrier to move transversely relative to the magnet holder. The image capturing device is disposed on the base and located above the platform for capturing at least one image of the coil carrier during the coil carrier is driven by the current device to move transversely relative to the magnet holder and for calculating displacement data of the coil carrier according to the at least one image. The collimator is disposed on the base for emitting light. The first half-reflecting mirror is disposed between the platform and the image capturing device and aligned with the collimator for reflecting light emitted by the collimator to the voice-coil-motor focusing device. The first reflecting mirror is detachably disposed on the voice-coil-motor focusing device for reflecting light reflected to the voice-coil-motor focusing device back to the first half-reflecting mirror. The optical sensing device is disposed on the collimator or disposed above the first half-reflecting mirror for detecting light reflected by the first reflecting mirror back to the first half-reflecting mirror during the coil carrier is driven by the current device to move transversely relative to the magnet holder to calculate tilt-angle data of the coil carrier.

In the measuring apparatus of the present invention, the optical sensing device is disposed on the collimator to detect light sequentially reflected by the first reflecting mirror and the first half-reflecting mirror during the coil carrier is driven by the current device to move transversely relative to the magnet holder for calculating the tilt-angle data of the coil carrier.

In the measuring apparatus of the present invention, the optical sensing device includes a second half-reflecting mirror, a second reflecting mirror, and an optical sensor. The second half-reflecting mirror is disposed between the image capturing device and the first half-reflecting mirror. The second reflecting mirror is adjacent to the second half-reflecting mirror. The optical sensor is disposed above the second reflecting mirror for detecting light passing through the first half-reflecting mirror and then being incident into the optical sensor via reflection of the second half-reflecting mirror and the second reflecting mirror during the coil carrier is driven by the current device to move transversely relative to the magnet holder, so as to calculate the tilt-angle data of the coil carrier.

The measuring apparatus of the present invention further includes an illumination device disposed on the image capturing device for providing light toward the voice-coil-motor focusing device.

In the measuring apparatus of the present invention, the first reflecting mirror is detachably disposed on the coil carrier.

In the measuring apparatus of the present invention, the voice-coil-motor focusing device further includes a lens assembly disposed in the coil carrier, and the first reflecting mirror is detachably disposed on the lens assembly.

The present invention further provides a measuring method for measuring a voice-coil-motor focusing device. The voice-coil-motor focusing device includes a magnet holder and a coil carrier. The coil carrier is movably disposed in the magnet holder. The measuring method includes placing the voice-coil-motor focusing device on a platform to be electrically connected to the a current device, disposing a first reflecting mirror detachably on the voice-coil-motor focusing device, a collimator emitting light to be reflected to the first reflecting mirror by a first half-reflecting mirror, an image capturing device capturing at least one image of the coil carrier during the coil carrier is driven by the current device to move transversely relative to the magnet holder, an optical sensing device detecting light reflected by the first reflecting mirror back to the first half-reflecting mirror during the coil carrier is driven by the current device to move transversely relative to the magnet holder, the image capturing device calculating displacement data of the coil carrier according to the at least one image, and the optical sensing device calculating tilt-angle data of the coil carrier according to the detected light.

In summary, the present invention utilizes the image capturing device to capture the images corresponding to the coil carrier during the coil carrier is driven by the current device to move transversely and utilizes the optical sensing device to detect light reflected back to the half-reflecting mirror, so as to calculate the displacement data and the tilt-angle data of the coil carrier respectively. In such a manner, after measuring the voice-coil-motor focusing device, the measuring apparatus provided by the present invention could precisely determine whether the performance of the anti-shake function of the voice-coil-motor focusing device conforms to its product needs according to the calculated displacement data and the calculated tilt-angle data of the coil carrier.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
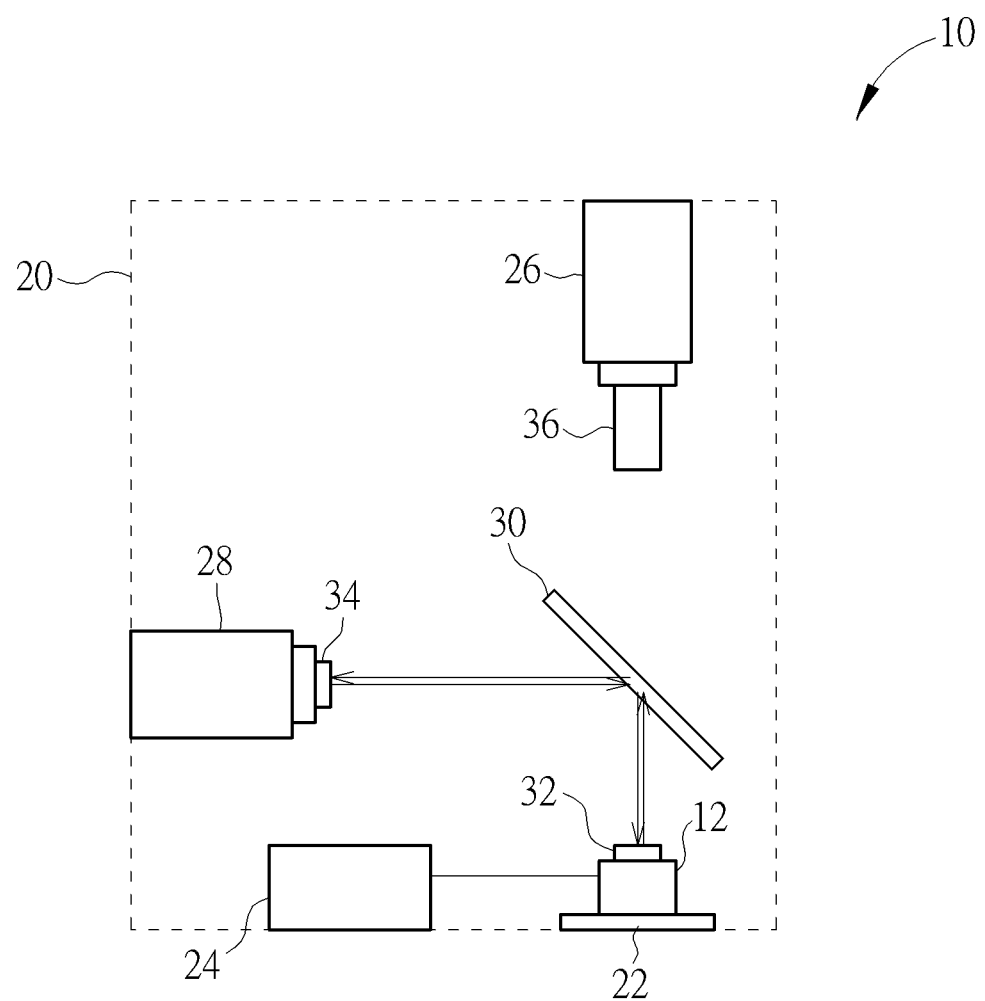
FIG. 1 is a diagram of a measuring apparatus measuring a voice-coil-motor focusing device according to an embodiment of the present invention.
Figure 2:
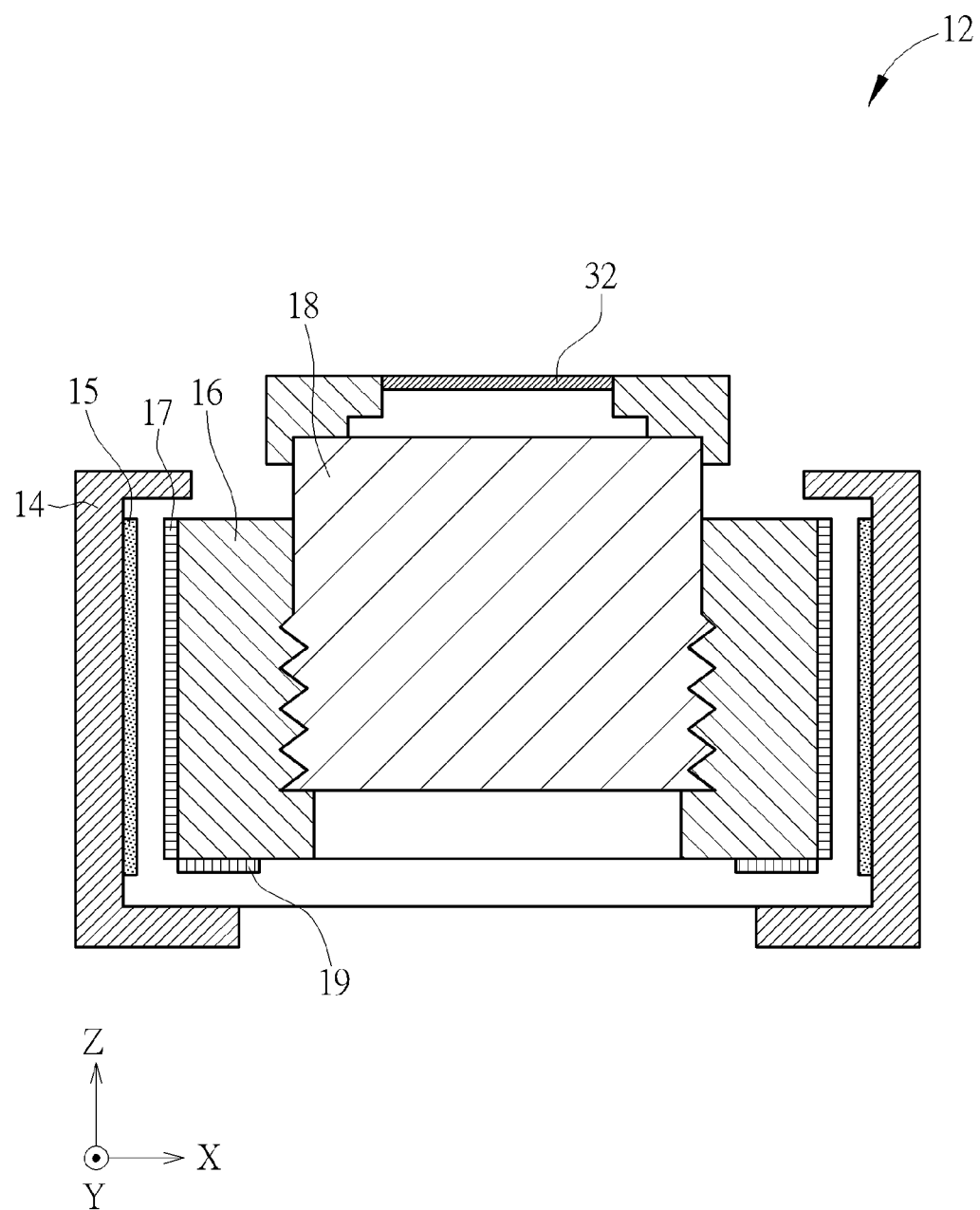
FIG. 2 is a sectional diagram of the voice-coil-motor focusing device in FIG. 1.

Please refer to FIG. 1 and FIG. 2. FIG. 1 is a diagram of a measuring apparatus 10 measuring a voice-coil-motor focusing device 12 according to an embodiment of the present invention. FIG. 2 is a sectional diagram of the voice-coil-motor focusing device 12 in FIG. 1. As shown in FIG. 1 and FIG. 2, the measuring apparatus 10 is used for measuring the voice-coil-motor focusing device 12 driven by current. The voice-coil-motor focusing device 12 includes a magnet holder 14, a coil carrier 16, and a lens assembly 18. The coil carrier 16 is movably disposed in the magnet holder 14. The lens assembly 18 is disposed in the coil carrier 16. As for the focusing design of the voice-coil-motor focusing device 12, it is commonly seen in the prior art. For example, once coils 17 wound around the coil carrier 16 (as shown in FIG. 2) are electrified, the coils 17 could receive force in a magnetic field generated by magnets 15 disposed on the magnet holder 14 to drive the coil carrier 16 to move longitudinally relative to the magnet holder 14 (i.e. along a Z-axis direction in FIG. 2). Accordingly, the position of the lens assembly 18 disposed on the coil carrier 16 could vary with longitudinal movement of the coil carrier 16, so as to achieve the autofocusing purpose. To be noted, the voice-coil-motor focusing device 12 is not limited to adopt the aforesaid design as shown in FIG. 2, meaning that the measuring apparatus provided by the present invention could be suitable for all voice-coil-motor focusing devices driven by current.

Description for the measuring design of the measuring apparatus 10 is provided as follows. In the displacement detecting design of the measuring apparatus 10, as shown in FIG. 1 and FIG. 2, the measuring apparatus 10 includes a base 20 (briefly depicted by dotted lines in FIG. 1), a platform 22, a current device 24, an image capturing device 26, a collimator 28, a half-reflecting mirror 30, a reflecting mirror 32, and an optical sensing device 34. The platform 22 is disposed on the base 20 for placing the voice-coil-motor focusing device 12. The current device 24 is electrically connected to the voice-coil-motor focusing device 12 for providing current to drive the coil carrier 16 to move transversely relative to the magnet holder 14. As for description for the current providing design and the related circuit design of the current device 24, it is commonly seen in the prior art and therefore omitted herein. The image capturing device 26 is disposed on the base 20 and is located above the platform 22. The image capturing device 26 could be a conventional image capturing apparatus (e.g. a charge-coupled device) for capturing images corresponding to the coil carrier 16 during the coil carrier 16 is driven by the current device 24 to move transversely relative to the magnet holder 14 and for calculating displacement data of the coil carrier 16 according to the captured images. In practical application, the measuring apparatus 10 could further include an illumination device 26 (e.g. a coaxial light source). The illumination device 36 is disposed on the image capturing device 26 for providing light toward the voice-coil-motor focusing device 12, so as to ensure that the image capturing device 26 could capture clear images to make the displacement data measured by the measuring apparatus 10 more accurate.

As for the tilt-angle detecting design of the measuring apparatus 10, it could be as shown in FIG. 1 and FIG. 2. The collimator 28 is disposed on the base 20 for emitting light. The half-reflecting mirror 30 is disposed between the platform 22 and the image capturing device 26 and is aligned with the collimator 28 for reflecting light emitted by the collimator 28 to the voice-coil-motor focusing device 12. In this embodiment, the reflecting mirror 32 is detachably disposed on the lens assembly 18 of the voice-coil-motor focusing device 12 and the optical sensing device 34 is disposed on the collimator 28. In such a manner, after the reflecting mirror 32 reflects light reflected to the voice-coil-motor focusing device 12 back to the half-reflecting mirror 30 and light is then reflected by the half-reflecting mirror 30 back to the collimator 28 so as to make light incident into the optical sensing device 34, the optical sensing device 34 could calculate tilt-angle data of the coil carrier 16 according to the detected light if tilt of the coil carrier 16 relative to the magnet holder 14 occurs while the coil carrier 16 is moving.

Figure 3:
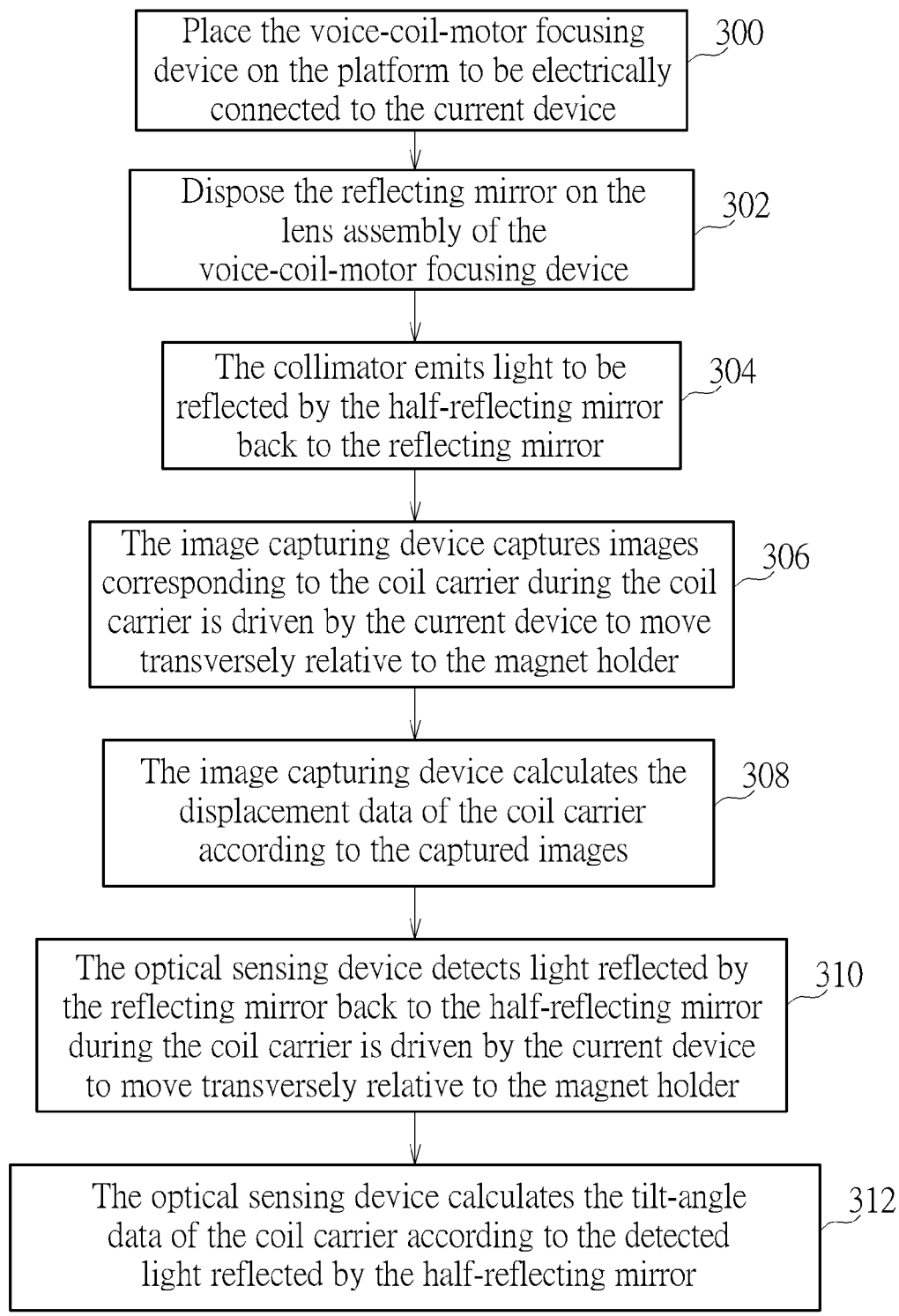
FIG. 3 is a flowchart of a measuring method for utilizing the measuring apparatus in FIG. 1 to measure the voice-coil-motor focusing device according to an embodiment of the present invention.

The measuring operations of the measuring apparatus 10 are described as follows. Please refer to FIG. 1, FIG. 2, and FIG. 3. FIG. 3 is a flowchart of a measuring method for utilizing the measuring apparatus 10 in FIG. 1 to measure the voice-coil-motor focusing device 12 according to an embodiment of the present invention. As shown in FIG. 3, the measuring method includes the following steps.

Step 300: Place the voice-coil-motor focusing device 12 on the platform 22 to be electrically connected to the current device 24;

Step 302: Dispose the reflecting mirror 32 on the lens assembly 18 of the voice-coil-motor focusing device 12;

Step 304: The collimator 28 emits light to be reflected by the half-reflecting mirror 30 back to the reflecting mirror 32;

Step 306: The image capturing device 26 captures images corresponding to the coil carrier 16 during the coil carrier 16 is driven by the current device 24 to move transversely relative to the magnet holder 14;

Step 308: The image capturing device 26 calculates the displacement data of the coil carrier 16 according to the capture images;

Step 310: The optical sensing device 34 detects light reflected by the reflecting mirror 32 back to the half-reflecting mirror 30 during the coil carrier 16 is driven by the current device 24 to move transversely relative to the magnet holder 14;

Step 312: The optical sensing device 34 calculates the tilt-angle data of the coil carrier 16 according to the detected light reflected by the half-reflecting mirror 30.

More detailed description for the aforesaid steps is provided as follows. As shown in FIG. 1, the voice-coil-motor focusing device 12 could be placed in the platform 12 to be electrically connected to the current device 24 (Step 300), and then the reflecting mirror 32 could be disposed on the lens assembly 18 (Step 302), so as to complete the placing operation of the voice-coil-motor focusing device 12. To be noted, in this embodiment, the present invention utilizes assembly of coils 19 and magnets 15 as shown in FIG. 2 to drive the coil carrier 16 to move transversely (i.e. along an X-axis direction or a Y-axis direction in FIG. 2) relative to the magnet holder 14 when the coils 19 are electrified, for achieving the anti-shake purpose. In brief, as shown in FIG. 2, the voice-coil-motor focusing device 12 could adopt the design in which the coils 19 are disposed on the bottom surface of the coil carrier 16, so that the measuring apparatus 10 could utilize the electrified coils 19 to receive force in the magnetic field generated by the magnets 15 for driving the coil carrier 16 to move transversely relative to the magnet holder 14.

Subsequently, the collimator 28 could emit light toward the half-reflecting mirror 30 so that the half-reflecting mirror 30 could reflect light to the reflecting mirror 32 (Step 304). Accordingly, the measuring apparatus 10 could establish the optical sensing mechanism for the voice-coil-motor focusing device 12 after light is reflected back to the half-reflecting mirror 30 by the reflecting mirror 32 and then is reflected back to the collimator 28 by the half-reflecting mirror 30 to be incident into the optical sensing device 34.

After the aforesaid steps are completed, the measuring apparatus 10 could utilize current provided by the current device 24 to drive the coil carrier 16 to move transversely relative to the magnet holder 14, and utilizes the image capturing device 26 and the optical sensing device 34 to measure transverse movement of the coil carrier 16 relative to the magnet holder 14. To be more specific, during the current device 24 provides current to drive the coil carrier 16 to move transversely relative to the magnet holder 14, the image capturing device 26 could capture images corresponding to the coil carrier 16 (Step 306) and then calculate the displacement data of the coil carrier 16. The image capturing device 26 could adopt a conventional image identification method to calculate the displacement data of the coil carrier 16. For example, the image capturing device 26 could capture a plurality of images corresponding to the coil carrier 16 during the coil carrier 16 moves transversely relative to the magnet holder 14 and then capture the contour of the coil carrier 16 in each captured image by image identification, so as to calculate the displacement data of the coil carrier 16 according to the result of comparing the contour of the coil carrier 16 in each captured image (Step 308). In such a manner, the present invention could utilize the displacement data of the coil carrier 16 as reference for estimating the performance of the anti-shake function of the voice-coil-motor focusing device 12. For example, the present invention could determine whether the coil carrier 16 moves to a correct position according to the displacement data of the coil carrier 16, or could accordingly establish relationship between current provided by the current device 24 and the displacement data of the coil carrier 16.

On the other hand, during the current device 24 provides current to drive the coil carrier 16 to move transversely relative to the magnet holder 14, the optical sensing device 34 could detect light reflected by the reflecting mirror 32 and the half-reflecting mirror 30 sequentially (Step 310), and could calculate the tilt-angle data of the coil carrier 16 according to the detected light (Step 312). The tile-angle calculating method is commonly seen in the prior art, and the related description is therefore omitted herein. In such a manner, the present invention could utilize the tilt-angle data of the coil carrier 16 as reference for estimating the performance of the anti-shake function of the voice-coil-motor focusing device 12. For example, the present invention could determine whether the coil carrier 16 is tilted according to the tilt-angle data of the coil carrier 16.

It should be mentioned that the lens assembly 18 is an omissible component. That is, in the embodiment in which the voice-coil-motor focusing device 12 has no lens assembly mounted thereon, the measuring apparatus 10 could only measure the coil carrier 16 having the reflecting mirror 32 mounted thereon. The measuring steps are reasoned by analogy according to the aforesaid embodiment, and the related description is omitted herein. Furthermore, the sequence of the aforesaid steps is not limited to FIG. 3, but varies with the practical application of the measuring apparatus 10. For example, the tilt-angle detecting steps of the measuring apparatus 10 (i.e. Step 310 and Step 312) could also be performed before the displacement measuring steps (i.e. Step 306 and Step 308), or could be performed with the displacement measuring steps at the same time.

Figure 4:
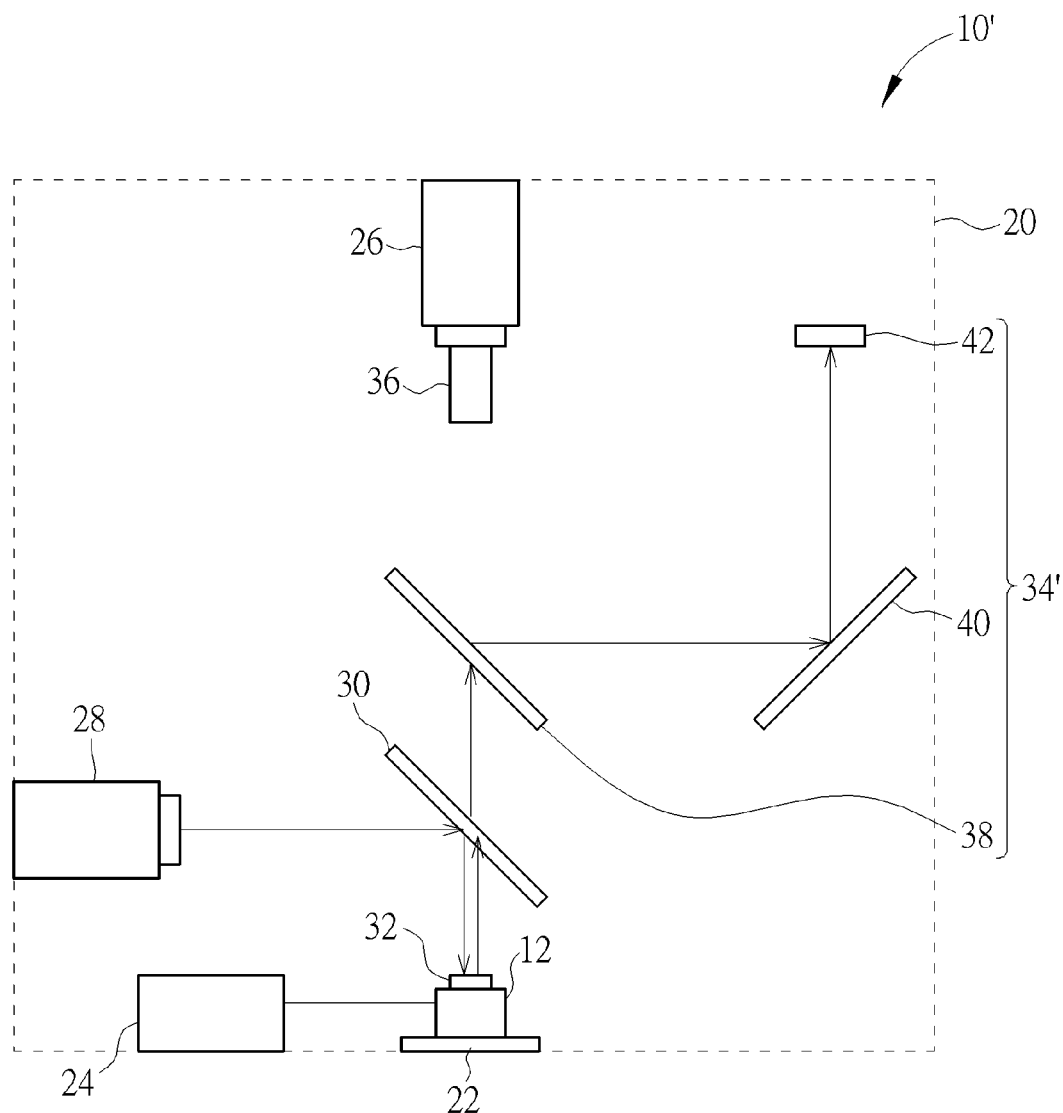
FIG. 4 is a diagram of a measuring apparatus measuring the voice-coil-motor focusing device according to another embodiment of the present invention.

Furthermore, the present invention could also calculate the tilt-angle data of the coil carrier by detecting light passing through the half-reflecting mirror. For example, please refer to FIG. 2 and FIG. 4. FIG. 4 is a diagram of a measuring apparatus 10' measuring the voice-coil-motor focusing device 12 according to another embodiment of the present invention. Components both mentioned in this embodiment and the aforesaid embodiment represent components with similar functions or structures, and the related description is omitted herein. As shown in FIG. 2 and FIG. 4, the measuring apparatus 10' is used for measuring the voice-coil-motor focusing device 12 driven by current. The measuring apparatus 10' includes the base 20 (briefly depicted by dotted lines in FIG. 4), the platform 22, the current device 24, the image capturing device 26, the collimator 28, the half-reflecting mirror 30, the reflecting mirror 32, and an optical sensing device 34'. In this embodiment, the optical sensing device 34' includes a half-reflecting mirror 38, a reflecting mirror 40, and an optical sensor 42. The half-reflecting mirror 38 is disposed between the image capturing device 26 and the half-reflecting mirror 30. The reflecting mirror 40 is adjacent to the half-reflecting mirror 38. The optical sensor 42 is disposed above the reflecting mirror 40. In such a manner, the optical sensor 42 could be used for detecting light passing through the half-reflecting mirror 30 and then being incident into the optical sensor 42 via reflection of the half-reflecting mirror 38 and the reflecting mirror 40 so as to calculate the tilt-angle data of the coil carrier 16. As for other description for the mechanical design and the measuring design of the measuring apparatus 10', it could be reasoned by analogy according to the aforesaid embodiment and therefore omitted herein.

In summary, the present invention utilizes the image capturing device to capture the images corresponding to the coil carrier during the coil carrier is driven by the current device to move transversely and utilizes the optical sensing device to detect light reflected back to the half-reflecting mirror, so as to calculate the displacement data and the tilt-angle data of the coil carrier respectively. In such a manner, after measuring the voice-coil-motor focusing device, the measuring apparatus provided by the present invention could precisely determine whether the performance of the anti-shake function of the voice-coil-motor focusing device conforms to its product needs according to the calculated displacement data and the calculated tilt-angle data of the coil carrier.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A measuring apparatus for measuring a voice-coil-motor focusing device, the voice-coil-motor focusing device comprising a magnet holder and a coil carrier, the coil carrier being movably disposed in the magnet holder, the measuring apparatus comprising:
   a base;
   a platform disposed on the base for placing the voice-coil-motor focusing device;
   a current device electrically connected to the voice-coil-motor focusing device for providing current to drive the coil carrier to move transversely relative to the magnet holder;
   an image capturing device disposed on the base and located above the platform for capturing at least one image of the coil carrier during the coil carrier is driven by the current device to move transversely relative to the magnet holder and for calculating displacement data of the coil carrier according to the at least one image;
   a collimator disposed on the base for emitting light;
   a first half-reflecting mirror disposed between the platform and the image capturing device and aligned with the collimator for reflecting light emitted by the collimator to the voice-coil-motor focusing device;
   a first reflecting mirror detachably disposed on the voice-coil-motor focusing device for reflecting light reflected to the voice-coil-motor focusing device back to the first half-reflecting mirror; and
   an optical sensing device disposed on the collimator or disposed above the first half-reflecting mirror for detecting light reflected by the first reflecting mirror back to the first half-reflecting mirror during the coil carrier is driven by the current device to move transversely relative to the magnet holder to calculate tilt-angle data of the coil carrier.

2. The measuring apparatus of claim 1, wherein the optical sensing device is disposed on the collimator to detect light sequentially reflected by the first reflecting mirror and the first half-reflecting mirror during the coil carrier is driven by the current device to move transversely relative to the magnet holder for calculating the tilt-angle data of the coil carrier.

3. The measuring apparatus of claim 1, wherein the optical sensing device comprises:
   a second half-reflecting mirror disposed between the image capturing device and the first half-reflecting mirror;
   a second reflecting mirror adjacent to the second half-reflecting mirror; and
   an optical sensor disposed above the second reflecting mirror for detecting light passing through the first half-reflecting mirror and then being incident into the optical sensor via reflection of the second half-reflecting mirror and the second reflecting mirror during the coil carrier is driven by the current device to move transversely relative to the magnet holder, so as to calculate the tilt-angle data of the coil carrier.

4. The measuring apparatus of claim 1 further comprising:
   an illumination device disposed on the image capturing device for providing light toward the voice-coil-motor focusing device.

5. The measuring apparatus of claim 1, wherein the first reflecting mirror is detachably disposed on the coil carrier.

6. The measuring apparatus of claim 1, wherein the voice-coil-motor focusing device further comprises a lens assembly disposed in the coil carrier, and the first reflecting mirror is detachably disposed on the lens assembly.

7. A measuring method for measuring a voice-coil-motor focusing device, the voice-coil-motor focusing device comprising a magnet holder and a coil carrier, the coil carrier being movably disposed in the magnet holder, the measuring method comprising:
   placing the voice-coil-motor focusing device on a platform to be electrically connected to the a current device;
   disposing a first reflecting mirror detachably on the voice-coil-motor focusing device;
   a collimator emitting light to be reflected to the first reflecting mirror by a first half-reflecting mirror, an image capturing device capturing at least one image of the coil carrier during the coil carrier is driven by the current device to move transversely relative to the magnet holder, and an optical sensing device detecting light reflected by the first reflecting mirror back to the first half-reflecting mirror during the coil carrier is driven by the current device to move transversely relative to the magnet holder;
   the image capturing device calculating displacement data of the coil carrier according to the at least one image; and
   the optical sensing device calculating tilt-angle data of the coil carrier according to the detected light.

8. The measuring method of claim 7, wherein the optical sensing device is disposed on the collimator, and the step of the optical sensing device detecting light reflected by the first reflecting mirror back to the first half-reflecting mirror during the coil carrier is driven by the current device to move transversely relative to the magnet holder comprises:
   the optical sensing device detecting light sequentially reflected by the first reflecting mirror and the first half-reflecting mirror back to the collimator during the coil carrier is driven by the current device to move transversely relative to the magnet holder for calculating the tilt-angle data of the coil carrier.

9. The measuring method of claim 7, wherein the optical sensing device comprises a second reflecting mirror, a second half-reflecting mirror, and an optical sensor, and the step of the optical sensing device detecting light reflected by the first reflecting mirror back to the first half-reflecting mirror during the coil carrier is driven by the current device to move transversely relative to the magnet holder comprises:
   the optical sensor detecting light passing through the first half-reflecting mirror and then being incident into the optical sensor via reflection of the second half-reflecting mirror and the second reflecting mirror during the coil carrier is driven by the current device to move transversely relative to the magnet holder, so as to calculate the tilt-angle data of the coil carrier.

10. The measuring method of claim 7 further comprising:
    an illumination device providing light toward the voice-coil-motor focusing device.

11. The measuring method of claim 7, wherein the step of disposing the first half-reflecting mirror detachably on the voice-coil-motor focusing device comprises:
    disposing the first reflecting mirror detachably on the coil carrier.

12. The measuring method of claim 7, wherein the voice-coil-motor focusing device further comprises a lens assembly disposed in the coil carrier, and the step of disposing the first half-reflecting mirror detachably on the voice-coil-motor focusing device comprises:

disposing the first reflecting mirror detachably on the lens assembly.

\* \* \* \* \*